United States Patent [19]

Markin

[11] Patent Number: 5,985,670
[45] Date of Patent: Nov. 16, 1999

[54] METHOD FOR AUTOMATIC TESTING OF LABORATORY SPECIMENS

[75] Inventor: Rodney S. Markin, Omaha, Nebr.

[73] Assignee: Board of Regents of the University of Nebraska, Lincoln, Nebr.

[21] Appl. No.: 08/910,834

[22] Filed: Aug. 13, 1997

Related U.S. Application Data

[63] Continuation of application No. 07/997,281, Dec. 23, 1992, abandoned.

[51] Int. Cl.⁶ .................................................. G01N 35/02
[52] U.S. Cl. ............................. 436/47; 422/65; 422/67; 436/48; 436/50; 436/55
[58] Field of Search ................. 436/47, 48, 50, 436/55; 422/63–65, 67

[56] References Cited

U.S. PATENT DOCUMENTS

| | | | |
|---|---|---|---|
| 3,533,744 | 10/1970 | Unger | 422/65 |
| 3,612,321 | 10/1971 | Larson | 422/67 |
| 3,660,638 | 5/1972 | Oberli | 422/66 |
| 3,751,958 | 8/1973 | Knedel et al. | 436/47 |
| 3,831,006 | 8/1974 | Chaffin, III et al. | 422/67 |
| 3,898,433 | 8/1975 | Sallet | 422/67 |
| 3,909,203 | 9/1975 | Young et al. | 422/67 |
| 3,916,157 | 10/1975 | Roulette et al. | 422/65 |
| 4,058,367 | 11/1977 | Gilford | 422/63 |
| 4,857,471 | 8/1989 | Salzman et al. | 422/65 |
| 5,100,622 | 3/1992 | Mimura et al. | 422/67 |

FOREIGN PATENT DOCUMENTS

| | | |
|---|---|---|
| 63-271164 | 11/1988 | Japan . |
| 1-301167 | 12/1989 | Japan . |
| 4204159 | 7/1992 | Japan . |

*Primary Examiner*—Jan Ludlow
*Attorney, Agent, or Firm*—Koley, Jessen, Daubman & Rupiper, P.C.; Mark D. Frederiksen

[57] ABSTRACT

A method for automatic testing of a laboratory specimen includes the initial step of obtaining a specimen to be tested and placing the specimen in a specimen container. The container is removably mounted in an independent carrier designed to carry an individual specimen through a laboratory to one or more of a plurality of work stations, where a predetermined test will be performed on the specimen. Once the test has been performed, the carrier is moved to another work station based on the result of the first test and then to an archiving station for storage of the specimen.

4 Claims, 1 Drawing Sheet

METHOD FOR AUTOMATIC TESTING OF LABORATORY SPECIMENS

CROSS-REFERENCE TO RELATED APPLICATION

This is a continuation of Ser. No. 07/997,281 filed Dec. 23, 1992 now abandoned.

TECHNICAL FIELD

The present invention relates generally to laboratory automation systems, and more particularly to an improved method for automating a laboratory for the testing of individual laboratory specimens.

BACKGROUND OF THE INVENTION

Clinical laboratory testing has changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform each test.

More recently, instruments have been developed to increase the efficiency of testing procedures by reducing turn around time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of the clinical laboratory. Known conveyor systems in the laboratory setting utilize separate conveyor segments to move specimens from a processing station to a specific laboratory work station. In order to obtain cost savings, the specimens are sorted manually, and grouped in a carrier rack to be conveyed to a specific location. In this way, a carrier will move a group of 5–20 specimens from the processing location to the specific work station to perform a single test on each of the specimens in the carrier.

While grouping a plurality of specimens in a single carrier may be more cost efficient where every specimen requires only a single specific test, and none of the specimens within a carrier require special priority, it is not uncommon in the hospital environment for a specimen to be subjected to a variety of different tests, or for a particular specimen to require a very short turn around time. In such an event, the current automation system could not be utilized, and the particular specimen would have to be manually moved to various work test stations based upon the time constraints and tests designated for the specimen.

Another problem with prior attempts at laboratory automation is in tracking the specimen and reporting the results of the specimen tested. Test results can serve as the basis for requiring additional testing of a particular specimen reflex or spawned testing. If the test results are required within a short time period, rapid and efficient reporting of test results can improve laboratory quality and efficiency.

SUMMARY OF THE INVENTION

It is a general object of the present invention to provide a method for automating a clinical laboratory which permits individual and independent assignment of a specimen to one or more of a plurality of work stations within the laboratory.

Another object of the present invention is to provide a method for automating a clinical laboratory which can improve turn around time for the testing of an individual specimen.

Still another object is to provide a method for automating a laboratory which permits automatic conveyance of a specimen to a plurality of work stations.

Still another object of the present invention is to provide a method for automating a clinical laboratory which tracks a specimen location throughout the laboratory and reports test results to a central database for immediate review by a doctor.

These and other objects will be apparent to those skilled in the art.

The method for automatic testing of a laboratory specimen of the present invention includes the initial step of obtaining a specimen to be tested and placing the specimen in a specimen container. The container is removably mounted in an independent carrier designed to carry an individual specimen of a number of different sizes and shapes through a laboratory to one or more of a plurality of work stations, where a predetermined test will be performed on the specimen. Once the carrier has arrived at the predetermined work station, the carrier is removed from the conveyor and a test is conducted on the specimen. The carrier is then returned to the conveyor and moved to an archiving station for storage of the specimen. Preferably, a computer is incorporated with the laboratory work stations, and includes a sensor located at each work station and archiving station. Each carrier and specimen container is marked with an identification code which is read by the sensor and transmitted to the computer. The computer may then operate a carrier removal apparatus at a predetermined work station to remove the carrier at the appropriate location for testing. Keyboards located at each work station permit the entry of test results at the work stations. After a particular test has been completed, the carrier is placed on the conveyor once again, and may be directed to an additional work station or to the archiving station. The conveyor system is preferably arranged in a closed loop formation such that a specimen can be moved to any specific work station in any specific sequence.

DESCRIPTION OF THE PREFERRED EMBODIMENT

Figure 1:
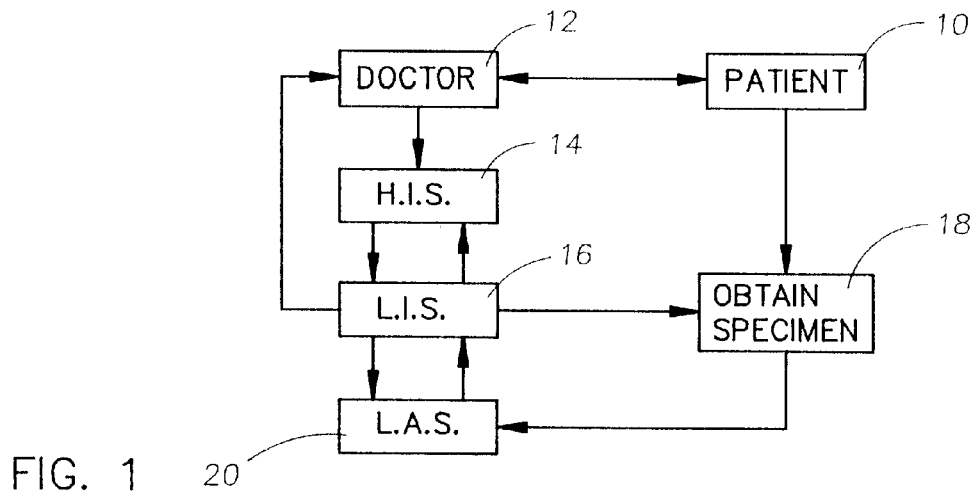
FIG. 1 is a flow chart showing the integration of a laboratory automation system with a laboratory information system and hospital information system.

Referring now to the drawings, FIG. 1 is a flowchart showing how the laboratory automation system (LAS) of the present invention integrates with the day-to-day operations of a hospital. Box 10 refers to any patient who is in need of examination and/or diagnosis. Box 12 represents the relevant physician or other practitioner who will interpret the results of the examination in order to determine the necessity of tests, in order to make a final diagnosis and/or prescribe a specified treatment. Information passes in both directions between doctor and patient during this examination.

As a result of the examination, the doctor will make a record of the examination results, and may enter a request for a specific test to be performed. This information is entered in the general hospital information system (HIS) shown as box 14 in the flowchart. The HIS will correlate patient identification information, room information, as well as any insurance or other typical general information necessary for operation of a hospital. The HIS is a computer system which communicates with various areas of the hospital to integrate all functions of the hospital.

Once the doctor's test order is correlated with the patient identification information, the HIS will forward the correlated information to the laboratory information system (LIS) designated as box 16 in the FIG. 1. The LIS is a computer system which is connected to the HIS to quickly and efficiently communicate information.

As shown in FIG. 1, the LIS assigns the task of obtaining a specimen to an appropriate technician, the retrieval of the specimen designated generally at box 18. The physical specimen obtained from the patient is then entered in the laboratory automation system (LAS) designated generally as box 20. The LAS takes the place of prior art manual testing procedures, including the reporting of the test results to the LIS. The LIS communicates with the LAS to order specific tests related to a specific specimen, and receive the results of those tests. The LIS also communicates with the HIS to report test results for accounting and insurance purposes. The LIS reports either to the doctor via a separate work station, or via the HIS, to report the results of the requested tests.

Figure 2:
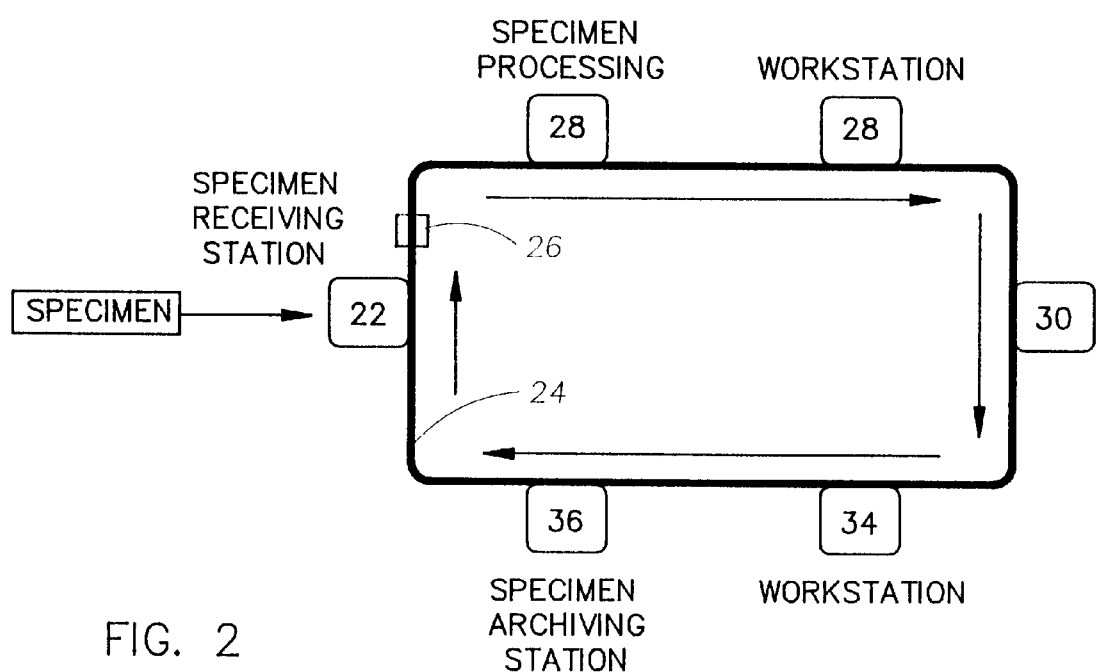
FIG. 2 is a schematic diagram of specimen movement through a laboratory automation system.

Referring now to FIG. 2, a schematic diagram of specimen movement throughout the laboratory automation system is shown. The specimen arrives at a specimen receiving station 22, where the specimen is entered on a conveyor system designated generally at 24. During the assignment of the task of obtaining a specimen, the laboratory information system would also provide a specimen container marked with an appropriate patient identification code. The inventor has found that a conventional bar code label applied to the specimen container is a simple and efficient method for fulfilling this function. Since most specimen containers are not designed for transport on a conveyor system, a separate carrier 26 is provided to support an individual specimen container on conveyor system 24. At specimen receiving station 22, the carrier 26 is given an identification code which correlates with the specimen container, so that the container and carriage may be directed throughout the laboratory automation system, even when the specimen container is removed from the carriage for specific testing at a work station.

As shown in FIG. 2, conveyor system 24 is preferably a continuously moving conveyor which will move carriers 26 in a generally closed loop system. The first station which a carrier 26 will encounter after entry on conveyor system 24, is specimen processing station 28. At processing station 28, the carrier assignment is entered into the LAS to determine which work stations the specimen must utilize, the order in which the stations are to be utilized and any other pertinent information with respect to priority or turn around time.

While FIG. 2 shows only 3 specific work stations, 30, 32, and 34, obviously a conventional clinical laboratory could have a wide variety of such stations throughout a facility. The closed loop system of conveyor 24 permits a specimen to stop at any given work station in any particular order.

Thus, if time constraints require that the test of work station 34 be performed first, and that a test of work station 32 be performed at some time after the test of work station 34, the specimen can travel on conveyor 24 past work stations 30 and 32, directly to work station 34, for immediate testing. Carrier 26 is then reintroduced on conveyor system 24 to follow the closed loop around to the next work station assigned to the specimen. Once the testing has been completed, the specimens are forwarded to the specimen archiving station 36 for removal from conveyor 24 and appropriate storage.

Figure 3:
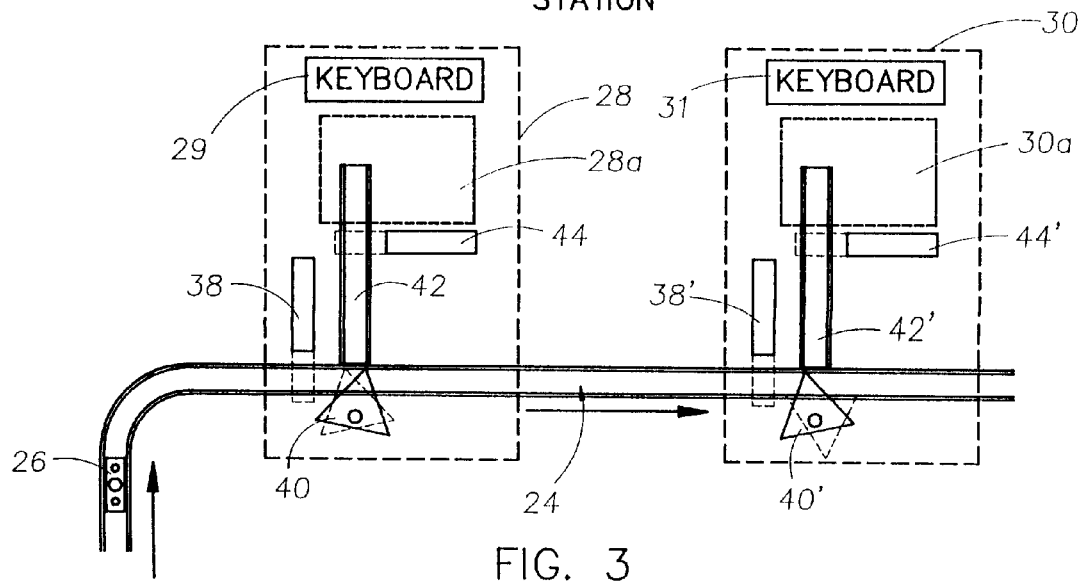
FIG. 3 is an enlarged schematic view of the specimen processing station and one work station along the schematic of FIG. 2.

Referring now to FIG. 3, an enlarged view of a portion of the schematic of FIG. 2 is shown. Specimen processing station 28 and work station 30 are shown in schematic view to demonstrate each specific work station located along conveyor system 24. As carrier 26 moves along conveyor 24, it will pass within the zone of specimen processing station 28 where a sensor 38 will detect the identification code on carrier 26. In the preferred embodiment of the invention, sensor 38 is a bar code reader while the identification code on the carrier 26 is a bar code. Sensor 38 is connected with the LIS, to record the movement of carrier 26. In the example of FIG. 3, carrier 26 has just entered the conveyor system 24, and therefore will be assigned to stop at the specimen processing station 28.

A gate 40 is connected to the LIS and will be activated to redirect the movement of carrier 26 off of conveyor 24 and on to an auxiliary conveyor 42 to reach the ultimate processing location 28a within the processing station 28. Processing area 28a may be comprised of manual processing, or fully automatic mechanical processing. An additional sensor 44 is positioned along auxiliary conveyor 42 to track the location of the carrier and specimen, and may be utilized to activate any automatic mechanical equipment associated with the specimen processing work area 28a.

As discussed above, the specimen processing station is utilized to direct the movement of the specimen to the appropriate work station at the appropriate time. A keyboard 29, or the like, is provided to enter the information into the LIS. This information is downloaded to the LIS which in turn distributes the appropriate instructions to the pertinent sensors and work stations, as described in more detail hereinbelow. Once processing has been completed, the specimen is again loaded in specimen carrier 26 and placed in conveyor system 24 by auxiliary conveyor 42. This procedure can be accomplished by virtue of sensor 44 or manually within the work area 28a of processing station 28.

In the present example, work station 30 has been designated as the first testing area for the specimen. Thus, conveyor 24 will move specimen carrier 26 into the zone of work station 30. A sensor 38' will acknowledge the passage of carrier 26 thereby, thereby triggering the LIS to direct gate 40' to divert the carrier 26 onto the auxiliary conveyor 42' of work station 30. A sensor 34' will then direct the specimen to the appropriate testing area 30a.

Once the test performed by work station 30 has been completed, the results are transmitted from the work area 30a to the LIS by virtue of keyboard 31, and the specimen is loaded in the specimen carrier 26 and positioned on auxiliary conveyor 42'. The specimen will then be moved to the main conveyor system 24 for movement to the next appropriate station. Work stations 32 and 34 are not shown in detail, but include the same basic equipment as work station 30. Thus, a sensor 38' located at work stations 32 and 34 will acknowledge passage of the specimen at that location and either direct the specimen into the work station, or direct the specimen to continue past the work station. If the order in which the tests are conducted is important, the specimen can be directed to bypass any work station along the conveyor system 24 so as to immediately reach the highest priority work station to perform the appropriate testing. Since the conveyor system is a closed loop, the specimen can then be moved around the loop to any other work station.

Once all requested tests have been performed, the specimen will be directed into the specimen archiving station utilizing a sensor 38' and gate 40' in the same manner as work stations 30, 32 and 34. Since every sensor 38, 38', 44 and 44' are interconnected by way of the laboratory information system, the location and status of any specimen is always readily accessible by the doctor. Since the LIS is programmable, the doctor can call for additional tests at any time during the movement of the specimen within the LAS. This ability to direct an individual specimen to one or more of a plurality of work stations decreases the turn around time and increases the versatility of the automation system. With the use of robotics, and a fully integrated laboratory instrumentation, it is possible to fully automate the entire laboratory automation system. In addition, the results of standard testing may conventionally require additional testing. In such a case, the LIS may automatically assign additional or different work station stops based upon the results received from a test at any given work station. The capability of prioritizing the testing, also permits a doctor to diagnose and/or otherwise individualize the test battery which is required for an individual patient.

Whereas the invention has been shown and described in connection with the preferred embodiment thereof, it will be understood that many modifications, substitutions and additions may be made which are within the intended broad scope of the appended claims. There has therefore been shown and described an improved method for automatic testing of laboratory specimen.

I claim:

1. A method of automatically testing and tracking a specimen in a laboratory, comprising the steps of:

placing a first specimen to be tested into a first specimen container;

marking the first container with a machine readable code;

marking a first carrier for transporting the first container with the same machine readable code as said first container, and placing the container thereon;

inputting information into a computer database relative to said first specimen, including information as to predetermined tests to be conducted on the specimen and the code marked on the container and carrier associated with the first specimen;

moving the first carrier on a conveyor among a plurality of work stations, said work stations adapted to conduct predetermined tests on specimens;

said computer tracking movement of said first carrier along said conveyor, and directing the movement of said first carrier according to information in the database regarding the first specimen, to predetermined work stations in a predetermined order to conduct predetermined tests;

inputting the results of tests conducted on said first specimen into said computer database;

said computer updating said database, with the first specimen test results, and directing movement of said first carrier to a different workstation of said plurality of workstations in response to said updated database; and said computer directing movement of said first carrier to an archiving station for storage of said first specimen, upon completion of all predetermined tests indicated in the database for said first specimen.

2. The method of claim 1, further comprising the steps of:

placing a second specimen to be tested into a second specimen container and marking the second container and a second carrier with a machine readable code, subsequent to the steps of placing said first specimen into said first container and marking the first container and said first carrier;

inputting information into the computer database relative to the second specimen, including information as to predetermined tests to be conducted on the second specimen and the code marked on the second container and the second carrier;

moving the second carrier on said conveyor among said work stations;

said computer tracking movement of said second carrier along said conveyor, and directing the movement of said second carrier according to said information in the database.

3. The method of claim 2, further comprising the step of inputting the results of tests conducted on said second specimen into said computer database, said computer updating said database, and the prior information in the database, with the second specimen test results, and directing movement of said second carrier to a different workstation of said plurality of workstations in response to said updated database.

4. The method of claim 3, further comprising the steps of said computer directing movement of said second carrier to the archiving station for storage of said second specimen, upon completion of all predetermined tests indicated in the database for said second specimen.

* * * * *